United States Patent [19]

Inamoto et al.

[11] 3,952,049
[45] Apr. 20, 1976

[54] DIESTERS OF TRICYCLIC ALCOHOLS

[75] Inventors: Yoshiaki Inamoto; Hirokazu Nakayama, both of Wakayama; Hidetsugu Takenaka, Arita; Takeji Kadono, Kainan, all of Japan

[73] Assignee: Kao Soap Co., Ltd., Tokyo, Japan

[22] Filed: Nov. 18, 1974

[21] Appl. No.: 524,657

Related U.S. Application Data

[62] Division of Ser. No. 173,666, Aug. 20, 1971, Pat. No. 3,862,206.

[30] Foreign Application Priority Data

Aug. 28, 1970 Japan.............................. 45-75410

[52] U.S. Cl........................... 260/485 L; 260/407; 260/475 FR; 260/475 SC
[51] Int. Cl.²................... C07C 69/34; C07C 69/60
[58] Field of Search ............................... 260/485 L

[56] References Cited
OTHER PUBLICATIONS
Bruson et al., J.A.C.S. 67, 723 (1945).

*Primary Examiner*—Lorraine A. Weinberger
*Assistant Examiner*—Jane S. Myers
*Attorney, Agent, or Firm*—Woodhams, Blanchard & Flynn

[57] ABSTRACT

A compound of the formula

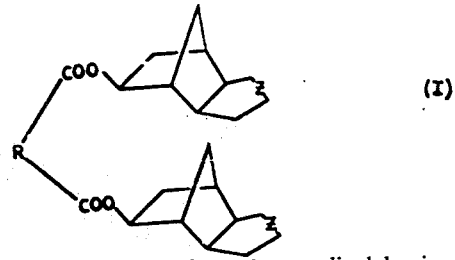

in which R is a divalent hydrocarbon radical having from 1 to 34 carbon atoms and Z represents a single or a double bond, is prepared by reacting (A) 2-exo-hydroxy-exo-trimethylenenorbornane or 2-exo-hydroxy-2,3,-dihydro-exo-dicyclopentadiene, with (B) a dibasic acid, or functional derivative thereof or an intramolecular cyclic anhydride thereof. The compounds are useful as ingredients for oiling agents for synthetic fibers, synthetic lubricants and oils and as ingredients for cosmetics, paints and inks.

8 Claims, No Drawings

DIESTERS OF TRICYCLIC ALCOHOLS

This is a division of application Ser. No. 173,666, filed Aug. 20, 1971, now U.S. Pat. No. 3,862,206.

BACKGROUND OF THE INVENTION

Field of the Invention

This invention relates to a process for preparing novel diesters of dicarboxylic acids with alcohols having a tricyclic hydrocarbon residue.

More specifically, this invention relates to a process for the preparation of dicarboxylic acid esters of alcohols derived from fully or partially hydrogenated exo-dicyclopentadienes, said dicarboxylic acid esters having the following formula:

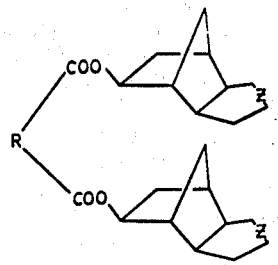

(I)

wherein Z represents a single or a double bond and R is a divalent hydrocarbon radical having from 1 to 34 carbon atoms.

Description of the Prior Art

Alcohols corresponding to the tricyclic hydrocarbon moieties in compounds of formula (I) prepared by the process of this invention, namely, 2-exo-hydroxy-exo-trimethylenenorbornane (Z = single bond) and 2-exo-hydroxy-2,3-dihydro-exo-dicyclopentadiene (Z = double bond), have been synthesized previously (H. A. Bruson and T. W. Riener, *J. Am. Chem. Soc.*, 67, 723 (1945)). However, the dicarboxylic acid esters of these alcohols are novel compounds which have not been described in the literature.

We have found that the above alcohols can be readily esterified with various dicarboxylic acids, or functional derivatives thereof, according to known techniques, and based on this finding, we have made the present invention.

SUMMARY OF THE INVENTION

An object of this invention is to provide a process for the preparation of dibasic acid esters of 2-exo-hydroxy-exo-trimethylenenorbornane or 2-exo-hydroxy-2,3-dihydro-exo-dicyclopentadiene of the formula

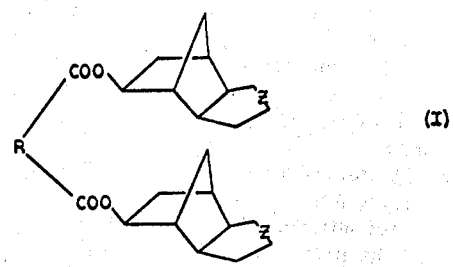

(I)

wherein R is a divalent hydrocarbon radical having 1 to 34 carbon atoms, and Z is a single or a double bond, which comprises reacting (A) a dibasic acid, or its functional derivative, of the formula

(II)

wherein R has the same meaning as defined above in formula (I) and X is hydroxyl, lower alkoxy having 1 to 6 carbon atoms or halogen, or an intramolecular cyclic anhydride of a dibasic acid of the formula

(III)

wherein R has the same meaning as defined above in formula (I), with (B) a tricyclic alcohol of the formula

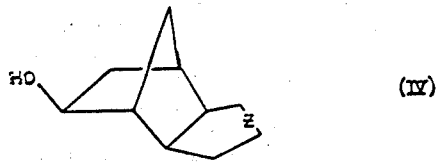

(IV)

wherein Z is a single or a double bond, to form a dibasic acid ester of 2-exo-hydroxy-exotrimethylenenorbornane (Z = single bond) or 2-exo-hydroxy-2,3-dihydro-exo-dicyclopentadiene (Z = double bond), which ester has the above formula (I).

The diesters prepared by the process of the present invention are novel substances which have not been synthesized heretofore.

Since these diesters contain a tricyclic hydrocarbon moiety in the molecule, they possess high heat stability, high oxidation stability and special physical properties, which are not found in conventional esters derived from aliphatic alcohols. Therefore, they are very useful as components of oiling agents for synthetic fibers, synthetic lubricants for various applications and synthetic lubricating oils, and as ingredients of cosmetics, paints, inks, etc.

As the dicarboxylic acid having a hydrocarbon radical of 1 through 34 carbon atoms, or its functional derivative, to be used in the process of this invention, there may be used (a) aliphatic saturated dicarboxylic acids and their functional derivatives such as malonic acid, succinic acid, glutaric acid, adipic acid, pimelic acid, suberic acid, azelaic acid, sebacic acid, halides and lower alkyl esters of these acids, and cyclic anhydrides of these acids, e.g., succinic anhydride and glutaric anhydride; (b) aliphatic unsaturated dicarboxylic acids and their functional derivatives such as maleic acid, fumaric acid, itaconic acid, citraconic acid, mesaconic acid, trans-glutaconic acid, cis-glutaconic acid, muconic acid, catalytically polymerized dimer acids, halides and lower alkyl esters of these acids, and cyclic anhydrides of these acids, e.g., maleic anhydride; (c) monocyclic saturated dicarboxylic acids and their functional derivatives such as various isomers of cyclopentane dicarboxylic acid and cyclohexane dicarboxylic acid, halides and lower alkyl esters of these acids, and cyclic anhydrides of these acids, e.g., 1,2-cyclohexanedicarboxylic anhydride; (d) monocyclic unsaturated dicarboxylic acids and their functional derivatives such as cyclohexane-(1)-1,2-dicarboxylic acid, its cyclic anhydride and thermally polymerized dimer acid; (e) polycyclic saturated dicarboxylic acids and their functional derivatives such as bicyclo-[2,2,1]-heptane-2,3-dicarboxylic acid, 1,3-dicarboxyadamantane, 1,3-bis(carboxymethyl)adamantane, and their halides, lower alkyl esters and cyclic anhydrides; (f) polycyclic unsaturated dicarboxylic acids and their functional derivatives such as bicyclo-[2,2,1]-heptene-(2)-5,6-dicarboxylic acid and its cyclic anhydride; and (g) monocyclic and polycyclic aromatic dicarboxylic acids and their functional derivatives such as phthalic acid, isophthalic acid, terephthalic acid, homophthalic acid, napthalene-2,6-dicarboxylic acid, their halides and lower alkyl esters, and their cyclic anhydrides, e.g., phthalic anhydride.

Dimer acids which are used in the present invention are $C_{36}$, long chain, aliphatic dibasic acids and are obtained by polymerizing a natural or synthetic, polymerizable unsaturated monobasic fatty acid having a hydrocarbon chain containing from 8 to 24 carbon atoms (usually 18 carbon atoms) in the molecule through a thermal polymerization or a catalytic polymerization process by using, for example, activated clay as a catalyst.

Usually, dimer acids can be obtained by the polymerization of drying or semi-drying oils, free fatty acids or simple aliphatic alcohol esters of these acids, for example, such starting materials rich in linoleic acid and linolenic acid. Suitable drying or semi-drying oils include soybean oil, linseed oil and cottonseed oil and suitable fatty acids include tall oil, soap stock etc. In the polymerization for producing dimer acids, most of the aliphatic acids having sufficient double bond functionalities combine to form mixtures of dibasic acid and higher polymerized fatty acids, probably by Diels-Alder mechanism. Examples of polymerization methods for producing dimer acids have been described in U.S. Pat. Nos. 2,793,219 and 2,793,222. Commercially available dimer acids consist of a major amount of dimer acid ($C_{36}$ long chain aliphatic dibasic acids) and a minor amount of trimer acids (similar $C_{54}$ tribasic acid) and some higher polymerized aliphatic acids and some residual monomers.

The novel products of this invention are prepared by reacting 2-exo-hydroxy-exo-trimethylenenorbornane or 2-exo-hydroxy-2,3-dihydro-exo-dicyclopentadiene with a dicarboxylic acid or its functional derivative, such as those mentioned above, in the presence or absence of a catalyst.

When a free dicarboxylic acid is used as one of the starting materials, the product can be prepared by heating the mixture of the dicarboxylic acid and the above alcohol in the presence of a catalyst. As catalysts effective for this reaction, there are included all of the known esterification catalysts, for instance, acid catalysts such as sulfuric acid, aliphatic and aromatic sulfonic acids and boron trifluoride, and neutral and basic catalysts such as oxides, hydroxides, carboxylates and lower alkoxides of alkali metals, alkaline earth metals, zinc, cadmium, tin, lead, antimony and bismuth.

The amount of the catalyst to be used for the above esterification reaction is in the range of 0.01 ~ 0.1 percent by weight, preferably 0.05 ~ 0.5 percent by weight, based on the total weight of both reactants.

In conducting the above esterification, the use of an excess of alcohol is advantageous for shortening the reaction time, but even if the alcohol is used in the stoichiometric amount of substantially two moles of alcohol per mole of dicarboxylic acid, the reaction proceeds very smoothly. The temperature used in the above esterification reaction is not substantially different from that used in the esterification of ordinary aliphatic alcohols. Namely, the above esterification can be conducted at a temperature in the range of from 30° to 300°C., preferably from 50° to 260°C. In oder to remove water formed in the reaction out of the reaction system, there may be employed any known technique such as distillation under reduced pressure, passage of an inert gas through the reaction system, use of an azeotropic dehydrating agent, etc.

When a halide of a dicarboxylic acid is used for the esterification reaction of this invention, the desired ester can be readily obtained by mixing and reacting the halide and the tricyclic alcohol. In this case, the reaction temperature is within the range of from −10° to 100°C., preferably from 0° to 50°C. and, in order to prevent undesirable formation of a tricyclic alkyl halide produced by the reaction of the hydrogen halide formed in the esterification with the starting tricyclic alcohol, the reaction mixture is cooled during the reaction to maintain it at a temperature not exceeding 100°C. The reaction is completed by gradually heating the reaction mixture after the evolution of the hydrogen halide has substantially ceased.

When a lower alkyl ester of a dicarboxylic acid is used as one of the starting materials, the reaction between said lower alkyl ester and the tricyclic alcohol is effected by heating a mixture of them in the presence of a so-called transesterification catalyst such as oxides, hydroxides, carboxylates and lower alkoxides of alkali metals, alkaline earth metals, zinc, cadmium, aluminum, silicon, titanium, tin, lead, antimony and bismuth. The lower alcohol resulting from the above transesterification reaction is removed from the reaction system to shift the equilibrium to the desired side. The removal of the lower alcohol may be accomplished most conveniently by distillation. The lower limit of the reaction temperature is the temperature sufficient to distill off the produced lower alcohol and the upper limit is 300°C., preferably 260°C. The boiling points of the tricyclic alcohols (above 270°C.) used in this invention are much higher than those of the lower alcohols resulting from the transesterification reaction, and therefore, the reaction can be accomplished very conveniently by the above procedure. When the above transesterification reaction is conducted in a current of an inert gas, such as nitrogen, not only is the coloration of the reaction mixture minimized, but also the removal of the lower alcohol produced in the reaction can be effected most conveniently.

The amount of the catalyst to be used for the transesterification reaction is within the range of from 0.01 to 1.0 percent by weight, preferably from 0.05 to 0.5 percent by weight, based on the total weight of the starting materials. Usually, the transesterification reaction is carried out by employing the tricyclic alcohol in an amount greater than the stoichiometric amount, namely, in an amount of at least 2.05 moles, preferably at least 2.2 moles, per mole of the dicarboxylic acid ester.

In the esterification reaction of this invention, there may also be used acid anhydrides. It is most preferable to use intramolecular cyclic anhydrides for the purpose of the present invention. So-called mixed acid anhydrides formed of two or more different carboxylic acids are not suitable at all for the purposes of this invention. When an intramolecular cyclic acid anhydride is used as one of the starting materials, the esterification can be accomplished by substantially the same procedure as that described for the esterification of free dicarboxylic acids. This is believed to be due to the fact that one of the carboxylic acid residues of the cyclic acid anhydride reacts spontaneously with 1 mole of the tricyclic alcohol, with the liberation of heat, to give a half ester of the dicarboxylic acid, while further esterification of said half ester to the intended diester of the general formula (I) requires the same reaction conditions as those adopted for converting the free dicarboxylic acid to the diester.

Further details of the present invention are described in the following illustrative examples. In the examples, the term "parts" refers to parts by weight unless otherwise indicated. All the melting points are uncorrected.

EXAMPLE 1

Preparation of bis(exo-trimethyleneorbornyl-(2)-exo) malonate (I; R = CH$_2$, Z = single bond).

A mixture of an alcoholic solution of sodium ethylate prepared by dissolving 0.1 part of metalic sodium in 10 parts by volume of ethanol, 48.0 parts of diethyl malonate and 118.7 parts of 2-exo-hydroxy-exo-trimethylenenorbornane was stirred at 150° – 170°C. for 5.5 hours, while a nitrogen gas stream was continuously passed through the reaction mixture, and the ethanol formed was continuously removed by distillation.

The reaction mixture was then cooled and dissolved in 300 parts by volume of benzene. The benzene solution was washed repeatedly with water until it became neutral, and then dried over anhydrous sodium sulfate. The benzene solution was distilled, and the fraction boiling at 200° – 205°C. (0.05 mm) was collected to give 100.5 parts (yield 90.0 percent) of bis(exo-trimethylenenorbornyl-(2)-exo) malonate with $n_D^{23.0}$ 1.5127.

| Saponification Value | Found: 300.4; Calculated: 301.4. |
|---|---|
| Acid Value | Found: 0; Calculated: 0. |
| Hydroxyl Value | Found: 2.0; Calculated: 0. |

Analysis: Found: C, 74.2; H, 8.5%. Calculated for C$_{23}$H$_{32}$O$_4$: C, 74.16; H, 8.66%.

IR spectrum (liquid film: cm$^{-1}$)

1750(s): $\nu_{C=O}$ ester

1270(s): $\nu_{as}$ } $\nu_{C-O-C}$ ester
1.50(s): $\nu_s$

NMR spectrum (CCl$_4$ solution, TMS as internal standard, $\tau$)

5.36–5.69 (undissolved resonance, 2H):

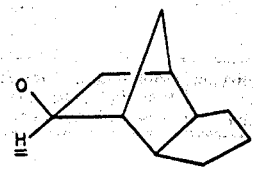

7.0 (s, 2H):

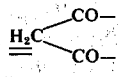

7.8–9.7 (complex m, 28H): Remaining hydrogens of the trimethylenenorbornane.

EXAMPLE 2

Preparation of bis(exo-trimethylenenorbornyl-(2)-exo) adipate (I; R = —(CH$_2$)$_2$—, Z = single bond).

In a flask equipped with the water separator described in Org. Syntheses, Coll. Vol. 3, p. 382, a mixture of 197.3 parts of adipic acid, 456.7 parts of 2-exo-hydroxy-exo-trimethylenenorbornane, 50 parts by volume of mixed xylene and 0.65 part of zinc oxide was refluxed with stirring at 230° – 250°C. under a nitrogen gas stream for 7 hours while separating and removing the water produced.

The reaction mixture was allowed to cool, and then was dissolved in 300 parts by volume of benzene. The benzene solution was washed with a saturated sodium hydrogen carbonate solution until it became alkaline, then with water until it became neutral, and then was dried over anhydrous sodium sulfate.

All of the low boiling fractions were distilled off from the above benzene solution maintained under a reduced pressure (0.4 mm) in a bath at 200°C., and the remaining viscous liquid was allowed to cool overnight in a refrigerator. The solidified bis(exo-trimethylenenorbornyl-(2)-exo) adipate, m.p. 87° – 88°C., obtained amounted to 516.6 parts (yield 92.3 percent).

| Saponification Value | Found: 270.4; Calculated: 270.7. |
|---|---|
| Acid Value | Found: 0.46; Calculated: 0. |
| Hydroxyl Value | Found: 0.21; Calculated: 0. |

Analysis: Found: C, 75.7; H, 9.2%. Calculated for C$_{26}$H$_{38}$O$_4$: C, 75.32; H, 9.24%.

IR spectrum (KBr; cm$^{-1}$)

1730(s): $\nu_{C=O}$ ester

1260(s): $\nu_{as}$ } $\nu_{C-O-C}$ ester
1170(s): $\nu_s$

NMR spectrum (CCl$_4$ solution, TMS as internal standard, $\tau$)

5.38–5.53 (undissolved resonance, 2H):

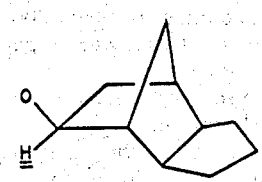

7.5–9.4 (complex m, 36H): remaining hydrogens of the trimethylenenorbornane and hydrogens of the adipic acid moiety.

EXAMPLE 3

Preparation of bis(exo-trimethylenenorbornyl-(2)-exo) sebacate (I; R = —(CH$_2$)$_8$—, Z = single bond).

In an apparatus like the apparatus used in Example 2, a mixture of 101.1 parts of sebacic acid, 163.5 parts of 2-exo-hydroxy-exo-trimethylenenorbornane, 31 parts by volume of mixed xylene and 0.26 part of zinc oxide was heated under reflux at 200° ~ 210°C. for 9 hours in a nitrogen gas stream while separating and removing the water produced.

The reaction mixture was treated in the same manner as in Example 2, and all the low boiling fractions were distilled off from the dried benzene solution to give 217.0 parts (yield 92.2 percent) of bis(exo-trimethylenenorbornyl-(2)-exo) sebacate, viscous liquid with $n_D^{20.0}$ 1.5018.

| Saponification Value | Found: 232.0; Calculated: 238.4. |
|---|---|
| Acid Value | Found: 1.5; Calculated: 0. |
| Hydroxyl Value | Found: 0.4; Calculated: 0. |

Analysis: Found: C, 75.9; H, 9.8%. Calculated for C$_{30}$H$_{46}$O$_4$: C, 76.55; H, 9.85%.

IR spectrum (liquid film; cm$^{-1}$)

1740(s): $\nu_{C=O}$ ester
1250(s): $\nu_{as}$ ⎫
1175(s): $\nu_s$ ⎭ $\nu_{C-O-C}$ ester NMR spectrum (CCl$_4$ solution, TMS as internal standard, $\tau$)

5.40–5.65 (undissolved resonance, 2H):

7.5–9.3(complex m, 44H): Remaining hydrogens of the trimethylenenorbornane and hydrogens of the sebacic acid moiety.

EXAMPLE 4

Preparation of bis(2,3-dihydro-exo-dicyclo-pentadienyl-(2)-exo) sebacate (I; R = —(CH$_2$)$_8$—, Z = double bond).

parts a similar apparatus as the one used in Example 2, a mixture of 30.3 arts of sebacic acid, 48.0 parts of 2-exo-hydroxy-2,3-dihydro-exo-dicyclopentadiene, 8.0 parts by volume of mixed xylene and 0.23 part of zinc oxide was heated under reflux at 200° ~ 205°C. for 22 hours in a nitrogen stream while separating and removing the water formed.

The benzene solution obtained by treating the reaction mixture in the same manner as in Example 2 was fractionally distilled and the fraction boiling at 238° ~ 243°C. (0.1 mm) was collected to give 51.2 parts (yield 73.2 percent) of bis(2,3-dihydro-exo-dicyclopentadienyl-(2)-exo) sebacate with $n_D^{22.5}$ 1.5102.

| Saponification Value | Found: 244.7; Calculated: 240.5. |
|---|---|
| Acid Value | Found: 7.9; Calculated: 0. |
| Hydroxyl Value | Found: 0.68; Calculated: 0. |
| Iodine Value | Found: 104.5; Calculated: 109.0. |

Analysis: Found: C, 76.9; H, 9.3; O, 13.6%. Calculated for C$_{30}$H$_{42}$O$_4$: C, 77.21; H, 9.07; O, 13.72%.

IR spectrum (liquid film; cm$^{-1}$)

3050(m): $\nu_{CH}$ (=CH—) ⎫
1620(w): $\nu_{C=C}$ ⎭

1735(s): $\nu_{C=O}$ ester

1250(s): $\nu_{as}$ ⎫
1170(s): $\nu_s$ ⎭ $\nu_{C-O-C}$ ester

NMR spectrum (CCl$_4$ solution, TMS as internal standard, $\tau$)

4.40 ⎫
4.61 ⎭ (AB-type q, J = 5 Hz, 4H):

5.25–5.56 (undissolved resonance, 2H):

7.0–9.2 (complex m, 34H): Remaining hydrogens of the dicyclopentadiene and hydrogens of the sebacic acid moiety.

EXAMPLE 5

Preparation of bis(exo-trimethylenenorbornyl-(2)-exo) maleate (I; R = ⌊—⌋ (cis); Z = single bond).

In a similar apparatus as the one used in Example 2, a mixture of 142.2 parts of maleic anhydride, 471.9 parts of 2-exo-hydroxy-exo-trimethylenenorbornane, 50 parts of volume of mixed xylene and 0.92 part of stannous oxide was heated under reflux at 220°C. for 5 hours in a nitrogen stream while separating and removing the water produced. The reaction mixture was cooled to below 100°C., mixed with 100 parts of warm water and refluxed with stirring for 30 minutes. The mixture was cooled and dissolved in 300 parts by volume of benzene, and the resulting small amount of precipitate was removed by filtration.

The aqueous layer was separated from the filtrate, and the benzene layer was treated in the same manner as in Example 2. All the low boiling fractions were distilled off from the resulting dried benzene solution to give 523.6 parts (yield 95.7%) of bis(exo-trimethylenenorbornyl-(2)-exo) maleate, viscous liquid with $n_D^{20}$ 1.5280.

| Saponification Value | Found: 274.3; Calculated: 291.8. |
|---|---|
| Acid Value | Found: 0.31; Calculated: 0. |
| Hydroxyl Value | Found: 0; Calculated: 0. |

IR spectrum (liquid film; cm$^{-1}$)

3040(m): $\nu_{CH}$ (=CH—)  
1640 : $\nu_{C=C}$  
1725 : $\nu_{C=O}$ ester  
1260 : $\nu_{as}$  
1155 : $\nu_s$ } $\nu_{C-O-C}$ ester

EXAMPLE 6

Preparation of bis(exo-trimethylenenorbornyl-(2)-exo) ester of catalytically polymerized dimer acid (I; R = C$_{34}$H$_{66}$, Z = single bond).

In a similar apparatus as the one used in Example 2, a mixture of 87.7 parts of catalytically polymerized dimer acid (saponification value 196, acid value 192), 69.4 parts of 2-exo-hydroxy-exo-trimethylenenorbornane, 30 parts by volume of mixed xylene and 0.31 part of zinc oxide was heated under reflux at 184° ~ 191°C. for 7.5 hours in a nitrogen stream while separating and removing the water produced. All the low boiling fractions were distilled off at 200°C. under 0.4 mm Hg from the dried benzene solution obtained by treating the reaction mixture in the same manner as in Example 2 to give 124.7 parts (yield 97.4 percent) of bis(exo-trimethylenenorbornyl-(2)-exo) ester of catalytically polymerized dimer acid in the form of a viscous liquid with $n_D^{22}$ 1.5012.

| Saponification Value | Found: 137.5; Calculated: 131.6. |
|---|---|
| Acid Value | Found: 1.2; Calculated: 0. |
| Hydroxyl Value | Found: 1.4; Calculated: 0. |

IR spectrum (liquid film; cm$^{-1}$)

1740(s): $\nu_{C=O}$ ester  
1250(s): $\nu_{as}$  
1170(s): $\nu_s$ } $\nu_{C-O-C}$ ester

EXAMPLE 7

Preparation of bis(exo-trimethylenenorbornyl-(2)-exo) 1,2-cyclohexanedicarboxylate (I; R =

Z = single bond).

In a similar apparatus as the one used in Example 2, a mixture of 23.1 parts of 1,2-cyclohexanedicarboxylic anhydride, 48.0 parts of 2-exo-hydroxy-exo-trimethylenenorbornane, 15 parts by volume of mixed xylene and 0.21 part of zinc oxide was heated under reflux at 200° ~ 230°C. for 75 hours in a nitrogen stream while separating and removing the water produced. The reaction mixture was cooled, mixed with 75 parts of water, refluxed for 30 minutes, cooled again and diluted with 200 parts by volume of benzene. The resulting benzene layer was separated, and was treated in the same manner as in Example 2. The dried benzene solution was fractionally distilled, and the collection of the fraction boiling at 225° ~ 228°C. (0.045 mm) gave 40.0 parts (yield 60.6 percent) of bis(exo-trimethylenenorbornyl-(2)-exo) 1,2-cyclohexanedicarboxylate, pale yellow, viscous liquid with $n_D^{24}$ 1.5187.

| Saponification Value | Found: 257.1; Calculated: 255.0. |
|---|---|
| Acid Value | Found: 4.9; Calculated: 0. |
| Hydroxyl Value | Found: 0; Calculated: 0. |

Analysis: Found: C, 7.61; H, 9.1; O, 14.8%. Calculated for C$_{28}$H$_{40}$O$_4$: C, 76.32; H, 9.15; O, 14.53%.

IR spectrum (liquid film; cm$^{-1}$)

1730(s): $\nu_{C=O}$ ester  
1250(s): $\nu_{as}$  
1170(s): $\nu_s$ } $\nu_{C-O-C}$ ester NMR spectrum (CCl$_4$ solution, TMS as internal standard, $\tau$)

5.39 ~ 5.65 (undissolved resonance, 2H):

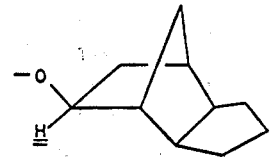

7.2 ~ 9.5 (complex $m$, 38H): Remaining hydrogens of the trimethylenenorbornane and hydrogens of the cyclohexane ring.

EXAMPLE 8

Preparation of bis(2,3-dihydro-exo-dicyclopentadienyl-)2)-exo) 1,2-cyclohexanedicarboxylate (I; R =

Z = double bond).

In a similar apparatus as the one used in Example 2, a mixture of 23.1 parts of 1,2-cyclohexanedicarboxylic anhydride, 48.0 parts of 2-exo-hydroxy-2,3-dihydro-exo-dicyclopentadiene, 7.0 parts by volume of mixed xylene and 0.21 part of zinc oxide was heated under reflux at 215°C. in a nitrogen stream for 41 hours while separating and removing the water produced. The reaction mixture was treated in the same manner as in Example 5. The resulting benzene solution was fractionated to give 48.0 parts (yield 74 percent) of bis(2,3-dihydro-exo-dicyclopentadienyl-2)-exo) 1,2-cyclohexanedicarboxylate, b.p. 226° − 230°C. (0.15 mm), $n_D^{22.5}$ 1.5280.

| Saponification Value | Found: 253.3; Calculated: 257.0. |
|---|---|
| Acid Value | Found: 2.3; Calculated: 0. |
| Hydroxyl Value | Found: 0; Calculated: 0. |
| Iodine Value | Found: 114.6; Calculated: 116.3. |

Analysis: Found: C, 77.0; H, 8.2; O, 14.6%. Calculated for C$_{28}$H$_{36}$O$_4$: C, 77.03; H, 8.31; O, 14.66%.

IR spectrum (liquid film; cm$^{-1}$)

1725(s): $\nu_{C=O}$ ester

1245(s): $\nu_{as}$  
1170(s): $\nu_s$  } $\nu_{C-O-C}$ ester

1620(m): $\nu_{C=C}$ 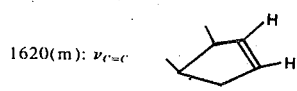

NMR spectrum (CCl$_4$ solution, TMS as internal standard, $\tau$)

4.33  
4.55 } (AB-type q, 4H): 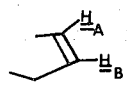

5.26 – 5.57 (undissolved resonance, 2H):

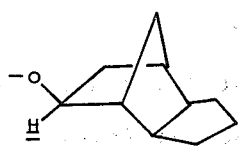

7.0 – 9.3 (complex m; 30H):   Remaining hydrogens of the dicyclopentadiene and hydrogens of the cyclohexane ring.

EXAMPLE 9

Preparation of bis(exo-trimethylenenorbornyl-(2)-exo) ester of thermally polymerized dimer acid (I; R = C$_{34}$H$_{64}$, Z = single bond).

A mixture 91.0 parts of thermally polymerized dimer acid dimethyl ester (saponification value 185, acid value 20), 69.4 parts of 2-exo-hydroxy-exo-trimethylenenorbornane, and 0.32 part of zinc acetate was heated with stirring at 200° – 210°C. for 14 hours in a nitrogen stream while separating and removing the methanol formed.

All the low boiling fractions were distilled off under a reduced pressure of 0.4 mm Hg at 200°C. from the dried benzene liquor obtained by treating the reaction mixture in the same manner as in Example 2 to give 125.6 parts (yield 98.4 percent) of bis(exo-trimethylenenorbornyl-)2) ester of thermally polymerized dimer acid, viscous liquid with $n_D^{18}$ 1.5049.

| Saponification Value | Found: 134.9; Calculated: 133.0. |
|---|---|
| Acid Value | Found: 2.1; Calculated: 0. |
| Hydroxyl Value | Found: 0.6; Calculated: 0. |

IR spectrum (liquid film; cm$^{-1}$)

1735(s): $\nu_{C=O}$ ester

1245(s): $\nu_{as}$  
1170(s): $\nu_s$  } $\nu_{C-O-C}$

EXAMPLE 10

Preparation of bis(exo-trimethylenenorbornyl-)2)-exo) biscyclo 2,2,1 heptane-2,3-dicarboxylate (I; R =

Z = single bond).

In a similar apparatus as the one used in Example 2, a mixture of 33.2 parts of bicyclo[2,2,1]heptane-2,3-dicarboxylic anhydride, 63.9 parts of 2-exo-hydroxy-exo-trimethylenenorbornane, 8.0 parts by volume of mixed xylene and 0.29 part of zinc oxide was heated under reflux at 200° – 220°C. in a nitrogen stream for 20 hours. The benzene solution obtained by treating the reaction mixture in the same manner as in Example 5 was fractionally distilled. Collection of the fraction boiling at 225° – 235°C. under 0.045 mm Hg gave 69.6 parts (yield 76.9 percent) of pale yellow, glassy solid of bis(exo-trimethylenenorbornyl-(2)-exo) bicyclo[2,2,1]heptane-2,3-dicarboxylate.

| Saponification Value | Found: 242.8; Calculated: 247.9. |
|---|---|
| Acid Value | Found: 1.1; Calculated: 0. |
| Hydroxyl Value | Found: 0; Calculated: 0. |

Analysis: Found: C, 76.9; H, 8.6; O, 13.9%. Calculated for C$_{29}$H$_{40}$O$_4$: C, 76.95; H, 8.91; O, 14.14%.

IR spectrum (liquid film; cm$^{-1}$)

1725(s): $\nu_{C=O}$ ester

1295(s): $\nu_{as}$  
1180(s): $\nu_s$  } $\nu_{C-O-C}$

EXAMPLE 11

Preparation of bis(exo-trimethylenenorbornyl(2)-exo) phthalate (I; R =

Z = single bond).

In a similar apparatus as the one used in Example 2, a mixture of 74.0 parts of phthalic anhydride, 197.6 parts of 2-exo-hydroxy-exo-trimethylenenorbornane, 26 parts by volume of mixed xylene and 0.3 part of stannous oxide was heated under reflux at 220° – 230°C. for 10 hours in a nitrogen stream, and the resulting reaction mixture was treated in the same manner as in Example 5. Any low boiling fractions were distilled off from the resulting benzene solution under reduced pressure of 0.4 mm Hg in a bath maintained at 200°C. to give 208.7 parts (yield 96.0 percent) of bis-(exo-trimethylenenorbornyl-(2)-exo) phthalate which solidified (m.p. 97° – 100°C) on standing overnight in a refrigerator.

| Saponification Value | Found: 225.4; Calculated: 258.2. |
|---|---|
| Acid Value | Found: 0.24; Calculated: 0. |
| Hydroxyl Value | Found: 2.2; Calculated: 0. |

Analysis: Found: C, 77.6; H, 7.8%. Calculated for C$_{28}$H$_{34}$O$_4$: C, 77.38; H, 7.89%.

IR spectrum (KBr; cm$^{-1}$)

1730(s): $\nu_{C=O}$ ester

1280(s): $\nu_{as}$ }
1125(s): $\nu_s$ } $\nu_{C-O-C}$

NMR spectrum (CCl₄ solution, TMS as internal standard, τ)
2.48 (m, 4H): hydrogens on the benzene nucleus
5.17 – 5.38 (undissolved resonance, 2H):

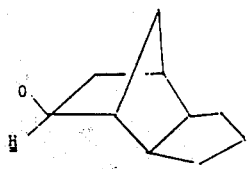

7.4 – 9.5 (complex m, 28H): Remaining hydrogens of the trimethylenenorbornane.

EXAMPLE 12

Preparation of bis(exo-trimethylenenorbornyl-(2)-exo) terephthalate (I; R —

Z — single bond).

A mixture of 58.4 parts of dimethyl terephthalate, 118.7 parts of 2-exo-hydroxy-exo-trimethylenenorbornane and 0.35 part of zinc acetate was heated at 230°C. in a nitrogen stream for 5.5 hours while distilling off methanol formed in the reaction. The reaction mixture was allowed to cool, and dissolved in 300 parts by volume of benzene. The benzene solution was treated in the same manner as in Example 1. All the low boiling fractions were distilled off under reduced pressure of 0.4 mm Hg in a bath maintained at 200°C. from the dried benzene solution to give 90.3 parts (yield 69.2 percent) of bis(exo-trimethylenenorbornyl-(2)-exo) terephthalate melting at 139.5° ~ 141.5°C.

| Saponification Value | Found: 256.8; Calculated: 258.2. |
| Acid Value | Found: 2.3; Calculated: 0. |
| Hydroxyl Value | Found: 1.8; Calculated: 0. |

Analysis: Found: C, 77.4; H, 7.7; O, 14.4%. Calculated for C₂₈H₃₄O₄: C, 77.39; H, 7.89; O, 14.73%.
IR spectrum (KBr; cm⁻¹)

1715(s): $\nu_{C=O}$ ester

1280(s): $\nu_{as}$ }
1125(s): $\nu_s$ } $\nu_{C-O-C}$

NMR spectrum (CDCl₃ solution, TMS as internal standard, τ)
1.95 (s, 4H): Hydrogen on the benzene nucleus
5.01 – 5.24 (undissolved resonance, 2H):

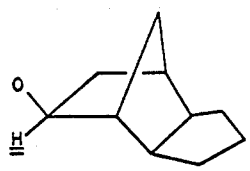

7.7 ~ 9.3 (complex m 28H): Remaining hydrogens of the trimethylenenorbornane.

EXAMPLE 13

Preparation of bis(exo-trimethylenenorbornyl-(2)-exo-oxycarbonylmethyl)adamantane (I; R =

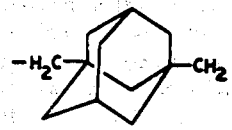

Z = single bond).

In a similar apparatus as the one used in Example 2, a mixture of 28.2 parts of 1,3-bis(carboxymethyl)adamantane, 37.2 parts of 2-exo-hydroxy-exo-trimethylenenorbornane, 8.0 parts by volume of mixed xylene and 0.2 part of zinc oxide was heated under reflux at 215° ~ 225°C. in a nitrogen stream for 6 hours. All the low boiling point fractions were distilled off from the dried benzene solution obtained by treating the reaction mixture in the same manner as in Example 2 to give 46.4 parts (yield 80.0 percent of 1,3-bis(exo-trimethylenenorbornyl-(2)-exo-oxycarbonylmethyl-)adamantane, colorless, viscous liquid with $n_D^{22}$ 1.5323.

| Saponification Value | Found: 213.5; Calculated: 215.5. |
| Acid Value | Found: 1.4; Calculated: 0. |
| Hydroxyl Value | Found: 0.37; Calculated: 0. |

Analysis: Found: C, 78.5; H, 9.2%. Calculated for C₃₄H₄₈O₄: C, 78.42; H, 9.29%.
IR spectrum (liquid film; cm⁻¹)

1730(s): $\nu_{C=O}$ ester

1225(m): $\nu_{as}$ }
1130(m): $\nu_s$ } $\nu_{C-O-C}$ ester

NMR spectrum (CCl₄ solution, TMS as internal standard, τ)
5.3 – 5.6 (undissolved resonance, 2H):

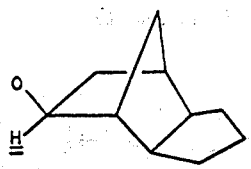

7.5 – 9.5 (complex m) }
7.96(s)

The signal at 7.96(s) is assigned to the tertiary hydrogens of the adamantane and the hydrogen adjacent to carbonyls (Ad—CH₂COO—).

EXAMPLE 14

Preparation of 1,3-bis(exo-trimethylenenorbornyl-(2)-exo-oxycarbonylmethyl)adamantane (I; R =

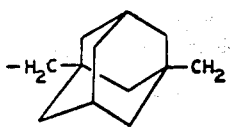

Z = single bond).

Twenty-five and two-tenths (25.2) parts of 1,3-bis(-carboxymethyl)adamantane was mixed with 119 parts of thionyl chloride, and the mixture was refluxed for 9.5 hours. The excess thionyl chloride was distilled off under a reduced pressure, and 50 parts by volume of benzene was added to the residue, any remaining thionyl chloride being distilled off azeotropically with benzene. This procedure was repeated three times to give thionyl chloride-free acid chloride, which was then dissolved in 20 parts by volume of benzene, and the resulting solution was maintained at a temperature below 10°C. by cooling in an ice bath. To the solution was added dropwise a mixture of 10 parts by volume of benzene and 30.4 parts of 2-exo-hydroxy-exo-trimethylenenorbornane. After completion of the addition, the mixture was stirred at room temperature for 3 hours, and the reaction temperature was gradually raised to 50°C. in a period of 1 hour, the reaction mixture being stirred at that temperature for a further period of 1 hour.

The resulting reaction mixture was treated in the same manner as in Example 2, and all the low boiling fractions were distilled off from the dried benzene solution to give 47.3 parts (yield 90.1 percent) of 1,3-bis-(exo-trimethylenenorbornyl-(2)-exo-oxycarbonylmethyl)adamantane with $n_D^{23}$ 1.5345.

| | |
|---|---|
| Saponification Value | Found: 212.8; Calculated: 215.5. |
| Acid Value | Found: 2.9; Calculated: 0. |
| Hydroxyl Value | Found: 0.1; Calculated: 0. |

Analysis: Found: C, 78.3; H, 9.1%. Calculated for $C_{34}H_{48}O_4$: C, 78.42; H, 9.29%.

IR spectrum (liquid film; cm$^{-1}$)

1730(s): $\nu_{C=O}$ ester

1225(m): $\nu_{as}$  
1130(s): $\nu_s$ } $\nu_{C-O-C}$ ester

NMR spectrum (CCl$_4$ solution, TMS as internal standard; $\tau$)

5.3 – 5.6 (undissolved resonance, 2H):

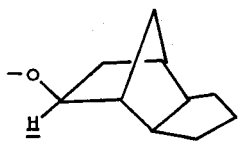

7.5 – 9.5 (complex m)  
7.96(s) } (46H):

The signal at 7.96(s) is assigned to the tertiary hydrogens of the adamantane and the hydrogens adjacent to carbonyl (Ad—C$\underline{H}_2$—COO—).

The embodiments of the invention in which an exclusive property or privilege is claimed are defined as follows:

1. A compound of the formula

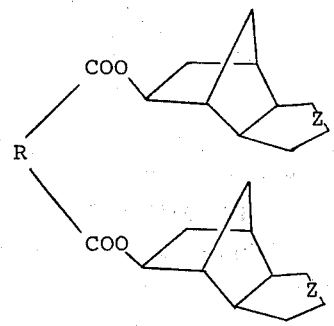

wherein Z is a single or double bond, and R is a divalent hydrocarbon moiety of a dicarboxylic acid selected from the group consisting of malonic acid, succinic acid, glutaric acid, adipic acid, pimelic acid, suberic acid, azelaic acid, sebacic acid, maleic acid, fumaric acid, itaconic acid, citraconic acid, mesaconic acid, trans-glutaconic acid, cis-glutaconic acid and muconic acid.

2. A compound as claimed in claim 1, in which R is a divalent hydrocarbon moiety of a dicarboxylic acid selected from the group consisting of malonic acid succinic acid, glutaric acid, adipic acid, pimelic acid, suberic acid, azelaic acid and sebacic acid.

3. A compound as claimed in claim 1, in which R is a divalent hydrocarbon moiety of a dicarboxylic acid selected from the group consisting of maleic acid, fumaric acid, itaconic acid, citraconic acid, mesaconic acid, trans-glutaconic acid, cis-glutaconic acid and muconic acid.

4. A compound as claimed in claim 1, bis(exo-trimethylenenorbornyl-(2)-exo) malonate.

5. A compound as claimed in claim 1, bis(exo-trimethylenenorbornyl-(2) adipate.

6. A compound as claimed in claim 1, bis(exo-trimethylenenorbornyl-(2)-exo) sebacate.

7. A compound as claimed in claim 1, bis(2,3-dihydro-exo-dicyclopentadienyl-(2)-exo) sebacate.

8. A compound as claimed in claim 1, bis(exo-trimethylenenorbornyl-(2)-exo) maleate.

* * * * *

UNITED STATES PATENT AND TRADEMARK OFFICE
CERTIFICATE OF CORRECTION

PATENT NO. : 3 952 049
DATED : April 20, 1976
INVENTOR(S) : Yoshiaki Inamoto et al It is certified that error appears in the above-identified patent and that said Letters Patent are hereby corrected as shown below:

Column 16, line 51; change "(2) adipate" to

---(2)-exo) adipate---.

Signed and Sealed this

Seventeenth Day of August 1976

[SEAL]

Attest:

RUTH C. MASON
*Attesting Officer*

C. MARSHALL DANN
*Commissioner of Patents and Trademarks*